United States Patent
Arthur et al.

(10) Patent No.: US 10,238,777 B2
(45) Date of Patent: Mar. 26, 2019

(54) HYDROPHOBIC POROUS NON MECHANICAL VALVE FOR MEDICAL SUCTION DEVICE

(71) Applicant: Porex Corporation, Fairburn, GA (US)

(72) Inventors: Michael Arthur, Douglasville, GA (US); Guoqiang Mao, Peachtree City, GA (US)

(73) Assignee: Porex Corporation, Fairburn, GA (US)

( * ) Notice: Subject to any disclaimer, the term of this patent is extended or adjusted under 35 U.S.C. 154(b) by 678 days.

(21) Appl. No.: 14/353,530

(22) PCT Filed: Nov. 1, 2012

(86) PCT No.: PCT/US2012/062943
§ 371 (c)(1),
(2) Date: Apr. 23, 2014

(87) PCT Pub. No.: WO2013/067106
PCT Pub. Date: May 10, 2013

(65) Prior Publication Data
US 2014/0296805 A1 Oct. 2, 2014

Related U.S. Application Data

(60) Provisional application No. 61/555,000, filed on Nov. 3, 2011.

(51) Int. Cl.
*A61M 1/00* (2006.01)
*A61M 5/165* (2006.01)
*A61M 39/20* (2006.01)

(52) U.S. Cl.
CPC ........ *A61M 1/0056* (2013.01); *A61M 1/0049* (2013.01); *A61M 1/0052* (2014.02);
(Continued)

(58) Field of Classification Search
CPC .............. A61M 1/0056; A61M 1/0052; A61M 1/0049; A61M 5/165; A61M 2039/205; A61M 2205/7536; A61M 2205/7563
(Continued)

(56) References Cited

U.S. PATENT DOCUMENTS 3,982,538 A  9/1976 Sharpe
4,443,515 A  4/1984 Atlas
(Continued)

FOREIGN PATENT DOCUMENTS

CN         101868262 A       10/2010
CN   ZL201280054098.8         4/2016
(Continued)

OTHER PUBLICATIONS

Office Action, Chinese Patent Application No. 201280054098.8, dated Jul. 9, 2015.
(Continued)

*Primary Examiner* — Andrew J Mensh
(74) *Attorney, Agent, or Firm* — Kilpatrick Townsend & Stockton LLP

(57) ABSTRACT

The present invention provides a porous non mechanical valve which retards or prevents the passage of bodily fluids and is resistant to being occluded or blocked by exposure to the surgical fumes or aerosols encountered during surgical procedures.

17 Claims, 14 Drawing Sheets

(52) U.S. Cl.
CPC ....... *A61M 5/165* (2013.01); *A61M 2039/205* (2013.01); *A61M 2205/7536* (2013.01); *A61M 2205/7563* (2013.01)

(58) Field of Classification Search
USPC ........................................................ 604/317
See application file for complete search history.

(56) References Cited

U.S. PATENT DOCUMENTS

| | | | |
|---|---|---|---|
| 4,487,606 A | 12/1984 | Leviton et al. | |
| 4,724,114 A | 2/1988 | McFarland et al. | |
| 4,820,577 A | 4/1989 | Morman et al. | |
| 5,053,132 A * | 10/1991 | Sirkar .................. | B01D 61/246 210/500.21 |
| 5,108,474 A | 4/1992 | Riedy et al. | |
| 5,175,046 A | 12/1992 | Nguyen | |
| 5,458,586 A | 10/1995 | Adiletta | |
| 5,750,585 A | 5/1998 | Park et al. | |
| 5,797,347 A | 8/1998 | Ochi | |
| 5,824,328 A | 10/1998 | Levy | |
| 5,836,929 A | 11/1998 | Bewick-Sonntag et al. | |
| 5,939,086 A | 8/1999 | Levy | |
| 5,998,032 A | 12/1999 | Hansen et al. | |
| 6,780,309 B2 * | 8/2004 | Haldopoulos ....... | A61M 1/0001 210/416.1 |
| 8,141,717 B2 | 3/2012 | Wingo et al. | |
| 2003/0099576 A1 | 5/2003 | Li et al. | |
| 2008/0197065 A1 * | 8/2008 | Wingo .............. | B01D 39/1661 210/198.2 |
| 2009/0071911 A1 * | 3/2009 | Folden ................ | A61M 1/3627 210/767 |
| 2012/0076708 A1 | 3/2012 | Ferri et al. | |

FOREIGN PATENT DOCUMENTS

| | | |
|---|---|---|
| EP | 1559442 | 8/2005 |
| EP | 2221075 | 8/2010 |
| JP | 2010-501664 A | 1/2010 |
| JP | 2010-538801 A | 12/2010 |
| WO | 8700439 | 1/1987 |
| WO | 0236708 | 5/2002 |
| WO | 2008/021539 A2 | 2/2008 |
| WO | 2009/039259 A1 | 3/2009 |
| WO | 2013067106 | 5/2013 |

OTHER PUBLICATIONS

Office Action, Japanese Patent Application No. 2014-540062, dated Mar. 15, 2016.
European Search Report, European Patent Application No. 15189580.2, dated Apr. 20, 2016, 6 pages.
Office Action, Japanese Patent Application No. 2014-540062, dated Jul. 26, 2016, 3 pages.
Ichikawa et al., "Superabsortive Polymers", Concise Polymeric Materials Encyclopedia, 1999, pp. 1523-1524.
International Application No. PCT/US2012/062943, "International Search Report and Written opinion", dated Apr. 19, 2013, 11 Pages.
Notification to Grant Patent Right for Invention, Chinese Patent Application No. 201280054098.8, dated Mar. 4, 2016.
Decision to Grant, Japanese Patent Application No. 2014-540062, dated Dec. 13, 2016, 3 pages.

* cited by examiner

HYDROPHOBIC POROUS NON MECHANICAL VALVE FOR MEDICAL SUCTION DEVICE

PRIOR RELATED APPLICATIONS

This application is a U.S. national phase patent application under 35 U.S.C. 371 of International Patent Application No. PCT/US2012/062943, filed Nov. 1, 2012, which claims benefit of priority of U.S. Provisional Patent Application No. 61/555,000 filed on Nov. 3, 2011, each of which is incorporated by reference herein in its entirety.

FIELD OF THE INVENTION

The present invention is in the field of hydrophobic porous non mechanical valves. These valves may be used in medical suction devices and they retard or prevent premature shut off of the devices upon exposure to surgical smoke, aerosols or bodily fluids.

BACKGROUND OF THE INVENTION

Non mechanical valves or filters have been widely used in suction devices for aspirating bodily fluids. These devices are generally made from sintered porous plastic comprising a water absorbable agent such as a super absorbent material to prevent bodily fluids from entering the vacuum system. Some examples of these devices are provided in WO87/00439 and U.S. Pat. Nos. 6,780,309 and 3,982,538.

These devices are generally filters employing a single part of a sintered product with uniform chemical composition, pore size and pore volume throughout the part, as in U.S. Pat. No. 6,780,309. This type of product can meet some application requirements, however it does not function well in certain applications, such as in surgeries that generate high concentrations of fumes or aerosols. The fumes often cause premature shut down of the vacuum system by clogging the filter. The premature clogging is caused by the particles or vapor in the fume generated during the surgical procedure. The filter will fail when encountering a relatively large amount of surgical fumes even though the filter has not contacted the body fluid which the filter is designed for. There is a need for a non mechanical valve that can withstand exposure to surgical fumes and aerosols and block the passage of bodily fluids.

In order to achieve good capability to block the passage of bodily fluids, sintered porous plastic non mechanical valves need to have a relatively small pore size. However, the small pore size may cause premature shut off of the vacuum suction canister when surgical fumes exist. Surgical fume contains organic particles, water, and organic vapors and aerosols generated during the surgery. These components in the surgical fume deposit on the non mechanical valve block the pores in the non mechanical valve, and cause the premature shut off of the vacuum suction canister.

Another drawback for currently available products is premature shut off when the suction during surgery generates liquid foams or bubbles. The foams or bubbles reach the non mechanical valve (filter) long before the liquid. The foams or bubbles will prematurely trigger the self-sealing action on current products and shut off the vacuum even though the liquid in the suction canister is very low.

The premature shut off of suction vacuum during surgery may have a life threatening impact, as the surgical field of view may be temporarily obscured to the surgeon. Further, such events increase the time in the operating room and increase costs. There is a need in the market for non mechanical valves that reduce premature shut off of the vacuum suction canister caused by fumes, liquid flush, foams or bubbles generated during surgery.

There is a need for a new non mechanical valve for medical suction devices that has high bulk liquid blocking capability and high bacterial aerosol filtration efficiency to prevent vacuum line contamination; and has high smoke, foam and liquid flushing tolerance to prevent premature shut-off during surgical procedures.

SUMMARY OF THE INVENTION

The present invention solves these problems by providing a porous non mechanical valve which retards or prevents the passage of bodily fluids and is resistant to being occluded or blocked by exposure to the surgical fumes or aerosols encountered during surgical procedures. The porous non mechanical valves of the present invention reduce and/or prevent clogging and premature shut off of vacuum systems, such as vacuum canister systems. These valves decrease lost time in the operating room, increase patient safety, decrease costs and prevent contamination of vacuum systems used to aspirate bodily fluids.

Porous non mechanical valves of the present invention comprise at least two distinguishable components. Different embodiments of the two distinguishable components include: a) Two components having different pore structures; b) Two components having different chemical compositions; or c) Two components having different pore structures and different chemical compositions.

In one embodiment, the porous non mechanical valve comprises two components, one component having different pore structures than the other section. These valves are resistant to fumes or smoke and decrease premature pressure drops resulting in shutdown of the valve and the vacuum canister system.

In another embodiment, the porous non mechanical valve has an external component which is hydrophobic without self-sealing properties, surrounding an internal component which is self-sealing. In some embodiments, these valves may be co-molded wherein the hydrophobic external component is molded over on the internal self-sealing component.

In yet another embodiment, the porous non mechanical valve has a fluoropolymeric coating on its external surface which surrounds a self-sealing layer.

In another embodiment, the non mechanical valve comprises a self-sealing plastic layer. In this embodiment, the valve may be in a form which does not have a hollowed structure or central lumen. Such forms may take different shapes such as a disk, ellipsoid, block, or other form which fits into a suction canister or other suction device. This embodiment can have a layered structure, one layer comprises hydrophobic media without self-sealing media and another layer comprises self-sealing media. The hydrophobic layer faces the solution, smoke or vapor and self-sealing layer faces the vacuum line. The hydrophobic layer prevents premature sealing by bubbles or foam during the suction process and the self-sealing layer blocks bulk liquid from passing into the vacuum line. These two layers may have different colors for identifying the function and orientation. Two layers may also have similar or different pore sizes or porosities.

In some embodiments the porous non mechanical valves of the present invention generally have a substantially uniform wall thickness, although variations in wall thickness are encompassed within the scope of the invention. In one embodiment, the non mechanical valves are cylindrical in shape with a central lumen which is open on one end facing the vacuum source, and closed on the other end facing the fluid, fumes and aerosol droplets. The closed end can be comprised of a more permeable material which allows a higher flow rate through the part, enabling it to pass the fumes or smoke and prevent the premature shutdown of the vacuum system due to clogging of the non mechanical valve by the particles and vapor in the surgical fumes or smoke. This more permeable portion can have a self-sealing additive or it can be thicker to improve sealing ability.

Another objective of some embodiments, such as the porous non mechanical valve with hydrophobic non self-sealing external surface, is to prevent premature shutdown of the vacuum suction device by the flush of body fluids, the foams of body fluids or the burst of bubbles in the foam. The hydrophobic non-sealing external layer prevents flushed liquids, foams and bubbles from penetrating into the self-sealing internal area and prevents premature quick sealing that causes a rapid increase of back pressure and system shutdown.

In one embodiment, the non mechanical valves of the present invention are sintered and have a sintered porous matrix. In one embodiment, the sintered porous non mechanical valves comprise plastic particles and fluid absorbent particles, such as superabsorbent particles, and the valve comprises two regions having different pore structures. These plastic particles may comprise polyolefin, polyester or nylon. The fluid absorbent particles in this invention include polymers in particle form that can quickly dissolve in water and form high viscosity solutions or gels.

In another embodiment, the porous non mechanical valves of the present invention are not comprised of a sintered porous matrix made of plastic particles and superabsorbent particles. In one embodiment, the porous non mechanical valve comprises plastic fibers or plastic bicomponent fibers and superabsorbent fibers, such as extruded fiber tubes or rods comprising plastic fibers and superabsorbent fibers. Fiber based porous non mechanical valves are made through a pultrusion process with selected fiber combinations. In this embodiment, the porous non mechanical valve may be in the form of extruded fiber tubes or rods. In this embodiment, fiber based porous non mechanical valves are made through a pultrusion process with selected fiber combinations. A fiber based non mechanical valve provides high pore volume and high smoke tolerance.

The porous non mechanical valves of the present invention may further comprise a color change indicator, an anti-microbial, a disinfectant, a deodorant or a combination thereof.

Other objects and advantages of the invention will be apparent from the following summary and detailed description of the embodiments of the invention taken with the accompanying drawing figures.

BRIEF DESCRIPTION OF THE DRAWINGS

FIG. 6 B is a schematic representation of one non mechanical valve 61 of the present invention showing a component of high permeability material 63 and a component of low permeability material 65 surrounding a central cylindrical lumen 66.

DETAILED DESCRIPTION

Figure 1:
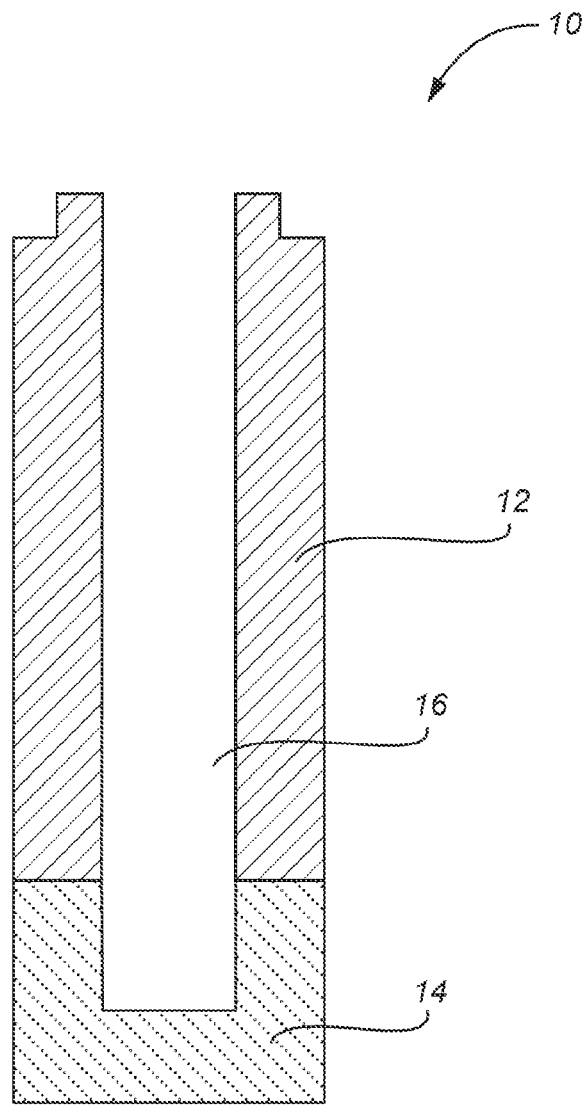
FIG. 1 is a schematic representation of one non mechanical valve 10 of the present invention showing a self-sealing component of low pore size 12 and a self-sealing component of high pore size 14 surrounding a central cylindrical lumen 16.

The present invention provides porous non mechanical valves which retard or prevent the passage of bodily fluids and are resistant to being occluded or blocked by exposure to the surgical fumes or aerosols encountered during surgical procedures.

The term high smoke tolerance in this application means the part will not significantly lose air flow or increase the pressure drop after passing air with significant smoke or aerosol.

The term high foam or liquid flushing tolerance in this application means the part will not significantly lose air flow or increase the pressure drop after exposure to the liquid foam or flushing of liquid.

The term self-sealing additives, including self-sealing particles and fibers, in this application include polymers that can absorb a large amount of water and form a high viscosity solution or gel.

The term self-sealing non-mechanical valve in this application includes valves that can block aqueous based liquid from passing through the valve, and significantly retard the passage of other gas media through the valve.

The term pore structure in this application includes but is not limited to pore size, pore volume and pore shape.

Porous non mechanical valves of the present invention comprise at least two distinguishable components. The two distinguishable components include: a) Two components having different pore structures; b) Two components having different chemical compositions; or c) Two components having different pore structures and different chemical compositions.

In one embodiment, the porous non mechanical valves of the present invention comprise two different components, each comprising a distinctive material composition, such that one component has a greater pore size than the other component. In one embodiment, the greater pore size material may have an increased amount of self-sealing additive. In another embodiment, the fluid entry sealing ability of the part is improved by increasing the thickness of the more permeable material In another embodiment, the porous non mechanical valves of the present invention comprise at least two distinguishable components which may include two components having different pore structures and having different chemical compositions. Porous non mechanical valves may also comprise more than two components.

In another embodiment, the porous non mechanical valves of the present invention comprise at least two distinguishable components. One component has a self-sealing chemical composition and the other component has no self-sealing composition.

In another embodiment, the porous non mechanical valves of the present invention comprise an internal component in contact with an external component. The external component has no self-sealing composition and the internal component has a self-sealing composition.

In another embodiment, the porous non mechanical valves of the present invention comprise at least two distinguishable components. One component is coated with a hydrophobic coating and the other component has no hydrophobic coating.

In yet another embodiment, the porous non mechanical valves of the present invention comprise an internal component in contact with an external component. The external component has the hydrophobic coating and the internal component has no hydrophobic coating. In one embodiment, the coating is a fluorinated polymer based coating.

In another embodiment, the porous non mechanical valves of the present invention comprise at least two distinguishable components. One component comprises a fiber based material and the other component comprises a sintered porous plastic based material. In a specific embodiment, the external component comprises fiber based materials and the internal component comprises a sintered porous plastic material incorporating a self-sealing composition.

In still another embodiment, the porous non mechanical valves of the present invention comprise at least two distinguishable components. One component comprises a fiber based material and the other component comprises a sintered porous plastic based material. In one embodiment, the external component comprises a sintered porous plastic material and the internal component comprises a fiber based material with a self-sealing composition.

Generally, porous non mechanical valves for use in suction canisters are hydrophobic and have the structure of a hollow cylinder with two ends, one open end and one closed end. This design is for assembly and air flow purposes.

Figure 11:
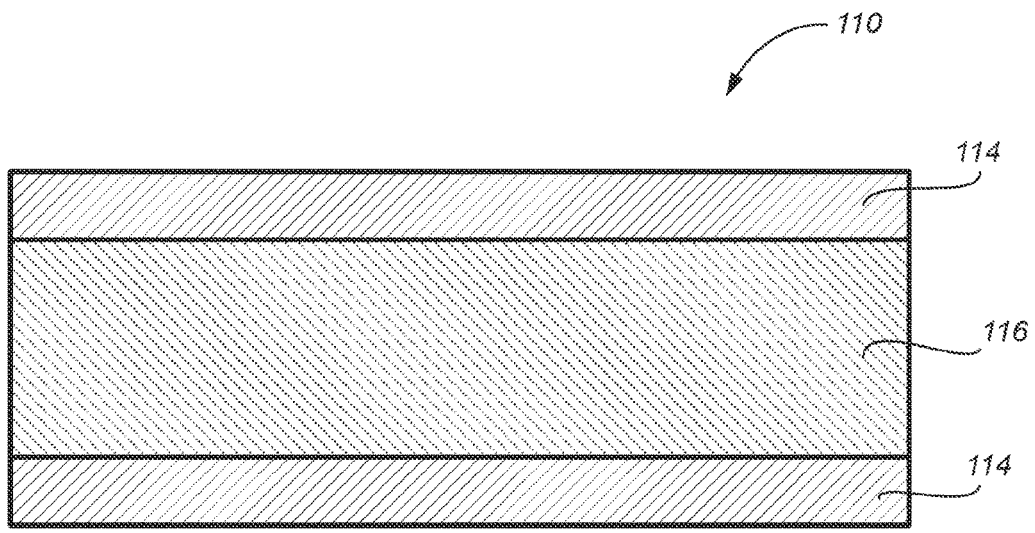
FIG. 11 is a schematic representation of a fiber non mechanical valve 110 with a layered structure. Non self-sealing fiber layers 114 are located on the external surfaces and the self-sealing fiber layer 116 is the middle layer.
Figure 12:
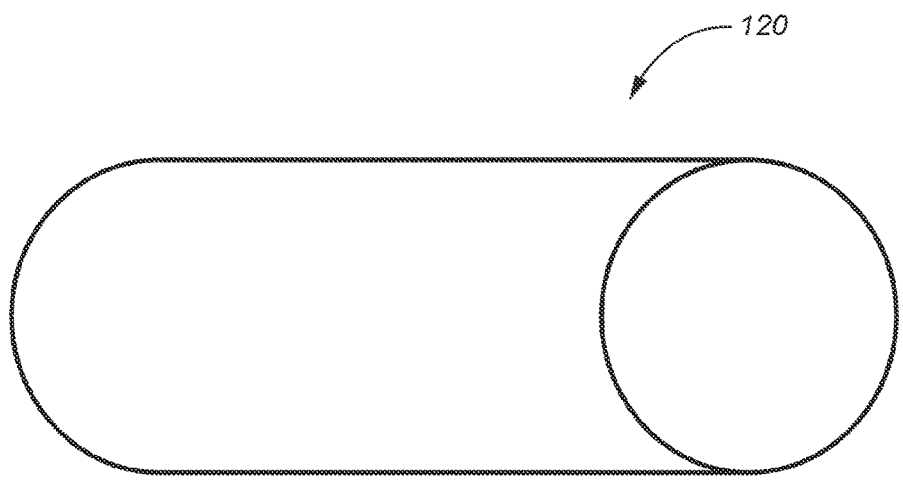
FIG. 12 is a schematic representation of a non mechanical valve 120 in the form of a self-sealing fiber rod.
Figure 13:
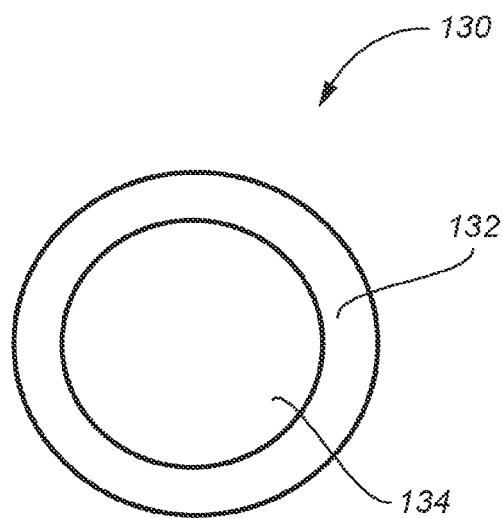
FIG. 13 is a cross-sectional schematic representation of fiber based non mechanical valve 130 in the form of a rod. The rod has a non self-sealing fiber sheath 132 and self-sealing fiber core 134.
Figure 14:
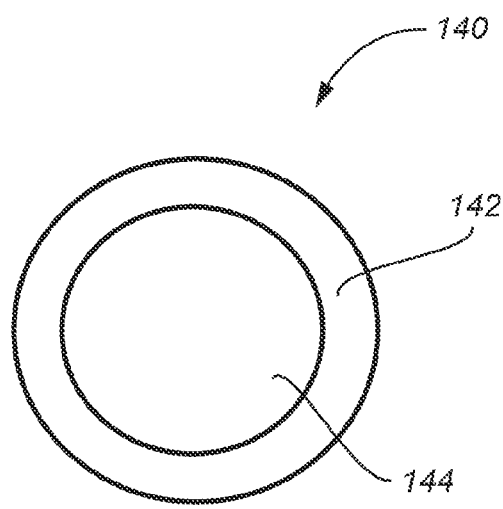
FIG. 14 is a cross-sectional schematic representation of a composite non mechanical valve 140 in the form of a rod. The rod has a non self-sealing sintered porous plastic sheath 142 and self-sealing fiber core 144.
Figure 15:
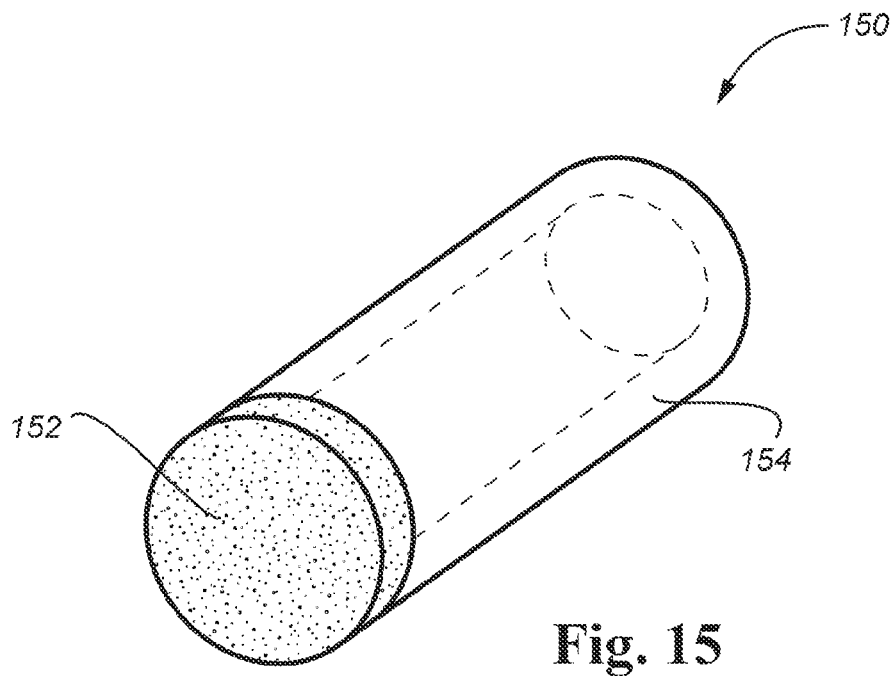
FIG. 15 is a schematic representation of a composite non mechanical valve 150. The valve has a self-sealing sintered porous plastic layer 152 covering one end of the self-sealing fiber tube 154.
Figure 16:
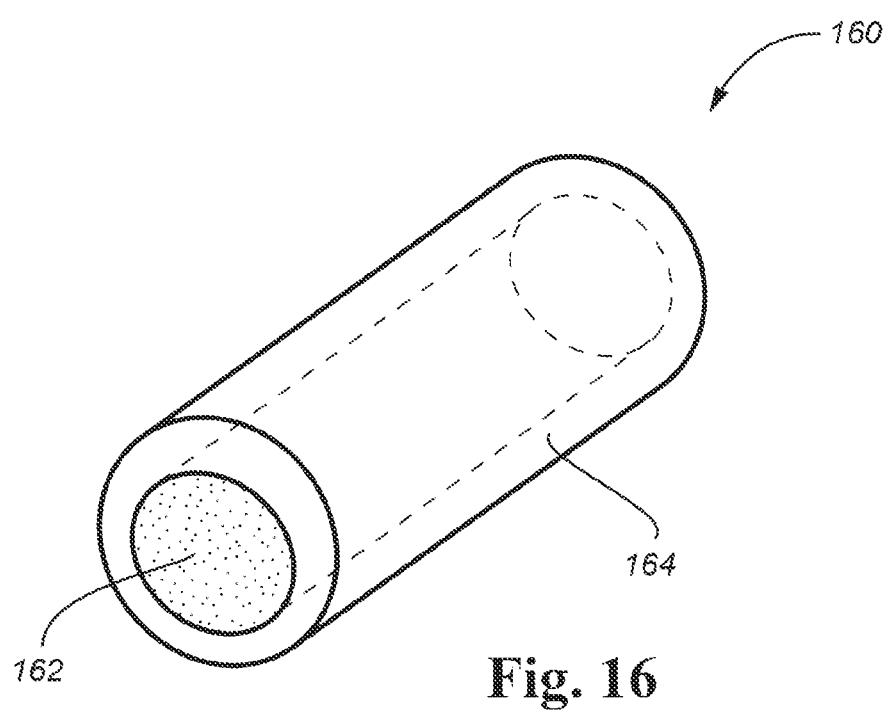
FIG. 16 is a schematic representation of a composite non mechanical valve 160. The valve has a self-sealing sintered porous plastic plug 162 in the lumen of one end of the self-sealing fiber tube 164.

The porous non mechanical valves of the present invention may have different shapes including but limited to cylindrical, tapered, layered, trapezoidal, spherical, or polygonal, depending on the application of the valve. In some embodiments, a lumen of some shape is located inside the valve so that air may pass into a collection system, such as a vacuum collection system. Some of these shapes are shown in the accompanying FIGS. 1-10 and 13-16. In other embodiments, the porous non mechanical valves of the present invention may not have a hollow structure and may be in the form of a rod or disk, for example as shown in FIG. 12. In yet other embodiments, the porous non mechanical valves of the present invention have a layered structure, for example as shown in FIG. 11.

The porous non mechanical valves of the present invention may have a hollowed structure or no hollowed structure as long as the non mechanical valves provide adequate air flow. These valves are resistant to fumes or smoke and decrease premature pressure drops resulting in a shutdown of the valve and the vacuum canister system.

In another embodiment, the non mechanical valve has an external component which is hydrophobic without self-sealing properties, surrounding an internal component art which is self-sealing. In some embodiments, these valves may be co-molded wherein the hydrophobic external component is molded over the internal self-sealing component.

In yet another embodiment, the non mechanical valve has a fluoropolymeric coating on its external surface which surrounds a self-sealing layer.

In another embodiment, the non mechanical valve comprises a self-sealing plastic layer. In this embodiment, the valve may be in a form which does not have a hollowed structure or central lumen. Such forms may take different shapes such as a disk, ellipsoid, block, or other form which fits into a suction canister or other suction device. This embodiment can have a layered structure, one layer comprises hydrophobic media without self-sealing media and another layer comprises self-sealing media. The hydrophobic layer faces the solution, smoke or vapor and the self-sealing layer faces the vacuum line. The hydrophobic layer prevents premature sealing by bubbles or foam during the suction process and the self-sealing layer blocks bulk liquid from passing into the vacuum line. These two layers may have different colors for identifying the function and orientation. Two layers may also have similar or different pore sizes or porosities.

The non mechanical valves of the present invention generally have a substantially uniform wall thickness, although variations in wall thickness are encompassed within the scope of the invention. In one embodiment, the non mechanical valves are generally cylindrical in shape with a central lumen which is open on one end facing the vacuum source, and closed on the other end facing the fluid and aerosol droplets. The closed end can be comprised of a more permeable material which allows a higher flow rate through the part, enabling it to pass the fumes or smoke and prevent the premature shut off of the vacuum system due to clogging of the non mechanical valve by the particles and vapor in the surgical fumes or smoke. This more permeable portion can have a self-sealing additive or it can be thicker to improve sealing ability.

In one embodiment, the non mechanical valves of the present invention are sintered and have a sintered porous matrix. In one embodiment, the sintered porous non mechanical valves comprise plastic particles and fluid absorbent particles and the valve comprises two regions having different pore structures. The fluid absorbent particles in this invention include polymers in particle form that can quickly dissolve in water and form high viscosity solutions or gels.

In another embodiment, the porous non mechanical valves of the present invention are not comprised of a sintered porous matrix made of plastic particles and superabsorbent particles. In one embodiment, the porous non mechanical valve comprises plastic fibers or plastic bicomponent fibers and superabsorbent fibers, such as extruded fiber tubes or rods comprising plastic fibers and superabsorbent fibers. Fiber based porous non mechanical valves are made through a pultrusion process with selected fiber combinations.

In one embodiment, the fiber based non mechanical valves of the present invention comprise plastic bicomponent binding fibers and superabsorbent fibers. Superabsorbent fibers absorb at least 10 times their weight in water. Superabsorbent fibers are used in an amount from about 5 to about 80 weight percent (wt % of the fiber product, about 10 to about 70 wt %, about 10 to about 60 wt %, or about 10 to about 50 wt %.

The present invention provides a method of reducing clogging of a vacuum suction device comprising: inserting the porous non mechanical valve of any of the preceding claims into the vacuum suction device; applying a vacuum across the porous non mechanical valve; and, permitting fluid or moisture to contact the porous non mechanical valve, wherein passage of the fluid or moisture through the porous non mechanical valve is retarded or prevented by the porous non mechanical valve.

The porous non-mechanical valves of the present invention may be used in any vacuum suction device. In one embodiment, the vacuum suction device is a medical vacuum suction device used in surgery.

Plastic Particles

In different embodiments, the plastic particles in the porous non mechanical valves comprise polyolefin, polyester or nylon. In one embodiment, the plastic particles in the porous non mechanical valve comprise a polyolefin. In some embodiments, a polyolefin comprises polyethylene, polypropylene, and/or copolymers thereof. Polyethylene, in one embodiment, comprises high density polyethylene (HDPE). In another embodiment, a polyolefin comprises ultrahigh molecular weight polyethylene (UHMWPE).

High density polyethylene, as used herein, refers to polyethylene having a density ranging from about 0.92 $g/cm^3$ to about 0.97 $g/cm^3$. In some embodiments, high density polyethylene has a degree of crystallinity (% from density) ranging from about 50 to about 90. Ultrahigh molecular weight polyethylene, as used herein, refers to polyethylene having a molecular weight greater than 1,000,000.

Some polymer particles that may be used in the present invention are also listed in WO02/36708.

Preferred porous matrices are made of organic polymers. Examples of organic polymers include, but are not limited to: atactic and syntactic homopolymers; statistical, random, and alternating copolymers; periodic, block, and graft copolymers; regular and irregular single-stranded and double-stranded polymers; and mixtures thereof. Examples of specific organic polymers include, but are not limited to, polyolefins, olefin copolymer rubber, ethylene-vinyl acetate copolymer, metallocene-catalyzed polyolefin copolymer, and mixtures thereof. Polyolefins include, but are not limited to, polymers of ethylene, propylene, 1-butene, butadiene, 1-pentene, 1-hexene, 1-octene, isoprene, 2-methyl-1-butene, 3-methyl-1-butene, 4-methyl-1-pentene, and mixtures thereof. Specific polyolefins include, but not limited to: polyethylene and polypropylene; polyesters; polyamides such as nylon; poly (ether sulfone); polytetrafluoroethylene; polyvinyl chloride; polycarbonates; and polyurethanes.

Porous matrices can be made of amorphous olefin copolymer rubbers and random elastic copolymers that comprise a crosslinked olefin as a major component. Examples of olefin copolymer rubbers include, but are not limited to: olefin copolymer rubbers lacking a diene component, such as ethylene-propylene copolymer rubber, ethylene-butene-1 copolymer rubber, and propylene-ethylene copolymer rubber; ethylene-propylene nonconjugated diene copolymer rubbers such as ethylene-propylene-cyclopentadiene copolymer rubber, ethylene-propylene-4-hexadiene copolymer rubber, ethylene-propylene-cyclooctadiene copolymer rubber, ethylene-propylene-methylenenorbonene copolymer rubber, and ethylene-propylene-ethylidenenorbonene copolymer rubber; ethylene-butadiene copolymer rubber; and mixtures thereof.

Porous matrices can further be made of metallocene catalyzed polyolefins, examples of which include, but are not limited to, low density polyethylene, linear low density polyethylene, medium density polyethylene, high density polyethylene, polypropylene, ethylene-propylene rubber, ethylene-propylene-diene terpolymer, ethylene-vinyl acetate copolymer, ethylene-maleic anhydride copolymer, ethylene-ethyl acetate copolymer, and mixtures thereof.

Self-Sealing Media, Superabsorbent Particles

Suitable water absorbable, gelling and super absorbent materials for use in the present invention are particles made of a polymer selected from the group consisting of: carboxyl methyl cellulose (CMC); hydroxypropyl cellulose (HPC); hydrolyzed starch; acrylonitrile graft copolymer; neutralized starch-acrylic acid graft copolymer; saponified acrylic acid ester-vinyl acetate copolymer; hydrolyzed acrylonitrile copolymer; acrylamide copolymer; modified cross-linked polyvinyl alcohol; neutralized self-crosslinking polyacrylic acid; crosslinked polyacrylate salts, neutralized crosslinked isobutylene-maleic anhydride copolymers, and salts and mixtures thereof, polyacrylic acids, sodium polyacrylic acid and the sodium salt of poly(2-propenamide-co-2-propenoic acid), alginates, Guar gum, Xanthan gum, Konjac gum, Tara gum or agars.

Materials that rapidly swell when contacted with water, but do not dissolve in water, are referred to herein as superabsorbent materials. Superabsorbent polymers can absorb large amounts of water and retain their structural integrity when wet. See Tomoko Ichikawa and Toshinari Nakajima, "Superabsortive Polymers" Concise Polymeric Materials Encyclopedia, 1523-1524 (Joseph C. Salamone, ed.; CRC; 1999). A variety of super-absorbent materials are known to those skilled in the art. For example, U.S. Pat. No.

5,998,032 describes superabsorbent materials and their use in feminine hygiene and medical articles. Other examples are disclosed by U.S. Pat. No. 5,750,585, which describes a water-swellable, super-absorbent foam matrix, and by U.S. Pat. No. 5,175,046, which discloses a super-absorbent laminated structure. Additional examples of super-absorbent materials include, but are not limited to, those disclosed in U.S. Pat. Nos. 5,939,086, 5,836,929, 5,824,328, 5,797,347, 4,820,577, 4,724,114, and 4,443,515.

Preferred liquid absorptive and super absorptive materials include preferred super-absorbent inclusions and particles made of a polymer selected from the group consisting of: carboxyl methyl cellulose (CMC); hydroxypropyl cellulose (HPC); hydrolyzed starch; acrylonitrile graft copolymer; neutralized starch-acrylic acid graft copolymer; saponified acrylic acid ester-vinyl acetate copolymer; hydrolyzed acrylonitrile copolymer; acrylamide copolymer; modified cross-linked polyvinyl alcohol; neutralized self-crosslinking polyacrylic acid; crosslinked polyacrylate salts, neutralized crosslinked isobutylene-maleic anhydride copolymers, and salts and mixtures thereof, polyacrylic acids, sodium polyacrylic acid and the sodium salt of poly(2-propenamide-co-2-propenoic acid), alginates, Guar gum, Xanthan gum, Konjac gum, Tara gum or agars.

Some of self-sealing additives, which are also called superabsorbent materials in this application, that may be employed in the present invention include, but are not limited to, cellulose based materials that will generate a high viscosity solution in water such as carboxymethylcellulose (CMC), Guar Gum, hydroxypropylcellulose (HPC), alginates, Xanthan gum, Konjac gum, Tara gum or agars and synthetic superabsorbent molecules such as acrylic acid based polymers, and acrylamide based polymers. These molecules will generate a viscous solution at a very low concentration. The materials required in this application will generally have a viscosity above 1000 cps in a 1% water solution. Other self-sealing additives which may be used in the present invention include, but are not limited to, inclusions and particles made of a polymer selected from the group consisting of: hydrolyzed starch acrylonitrile graft copolymer; neutralized starch-acrylic acid graft copolymer; saponified acrylic acid ester-vinyl acetate copolymer; hydrolyzed acrylonitrile copolymer; acrylamide copolymer; modified cross-linked polyvinyl alcohol; neutralized self-crosslinking polyacrylic acid; cross-linked polyacrylate salts, and neutralized cross-linked isobutylene-maleic anhydride copolymers, and salts and mixtures thereof.

Plastic Fibers

Porous fiber matrices may include plastic fibers. In one embodiment, the plastic fibers are plastic bicomponent binding fibers. Plastic bicomponent binding fibers in this application include, but are not limited to: polyethylene (PE)/polyethylene terephthalate (PET), polypropylene (PP)/PET, co-polyester/PET, PE/Nylon, PP/Nylon, Nylon/Nylon, PE/PP, and PET/PP fibers.

Self-Sealing Media, Superabsorbent Fibers

The superabsorbent fibers include, but are not limited to, polyacrylonitrile fibers, modified polyacrylonitrile fibers, polyacrylic acid based fibers, polyoxyalkylene glycol fiber and naturally based modified cellulose fibers. Super-absorbent fibers can rapidly swell when they absorb water, but are not readily soluble in water. Specific super-absorbent materials from which super-absorbent fibers can be made are capable of absorbing greater than about 100, 200, 500, or 1000 percent of their weight in water while maintaining their structural integrity. Consequently, and without being limited by theory, when specific materials of the invention are contacted with water the super-absorbent fibers they contain swell to block and/or inhibit the passage of both liquids and gases through them. When contacted with water, super-absorbent materials swell to form gels. Most super-absorbent polymers currently used are sodium acrylate-based polymers which have a three dimensional network-like molecular structure. Small amounts of crosslinkers play a major role in modifying the properties of superabsorbent polymers. The type and quantity of crosslinkers control both the swelling capacity and gel modulus. Other suitable water swelling materials are natural-based super-absorbent fibers such as, but not limited to, crosslinked polysaccharides or modified cellulose products. Still other super-absorbent materials that can be used to provide fibers useful in particular embodiments of this invention are described below, as are various fabric forms of such fibers. Superabsorbent fibers which may be employed are disclosed in US2003/0099576.

Acrylic acid based super-absorbent fibers can be made from ethylenically unsaturated carboxylic monomers and copolymerizable ethylenically unsaturated monomers. These fibers are formed by extruding a solution or dispersion of the polymeric material in a solution of the secondary matrix copolymer in its non-crosslinked state into a gaseous environment wherein solvent is removed to form the fiber, and subsequently crosslinking the matrix copolymer. Other super-absorbent fibers that can be used in this invention are bi-layer hydrolyzed polyacrylonitrile salt fibers which display a core/sheath structure bicomponent fiber, wherein the sheath is an outer layer of hydrolyzed polyacrylonitrile salt, such as, but not limited to, polysodium acrylate or polyammonium acrylate, and the core is polyacrylonitrile. Another type of super-absorbent fiber, hydrolyzed polysuccinimide, comprises partially hydrolyzed, internally plasticized, cross-linked, superabsorbing fibers derived from polysuccinimide fiber. The crosslinked hydrolyzed polysucinimide fibers are made of polyamide containing at least three divalent or polyvalent moieties distributed along the polymer chain. Specific examples of super-absorbent materials that can be provided as fibers and used in various embodiments of this invention include, but are not limited to, hydrolyzed starch acrylonitrile graft copolymer; neutralized starch-acrylic acid graft copolymer; saponified acrylic acid ester-vinyl acetate copolymer; hydrolyzed acrylonitrile copolymer; acrylamide copolymer; modified cross-linked polyvinyl alcohol; neutralized self-crosslinking polyacrylic acid; crosslinked polyacrylate salts; neutralized crosslinked isobutylene-maleic anhydride copolymers; and salts and mixtures thereof.

Fluorinated Polymer Coating.

Figure 3:
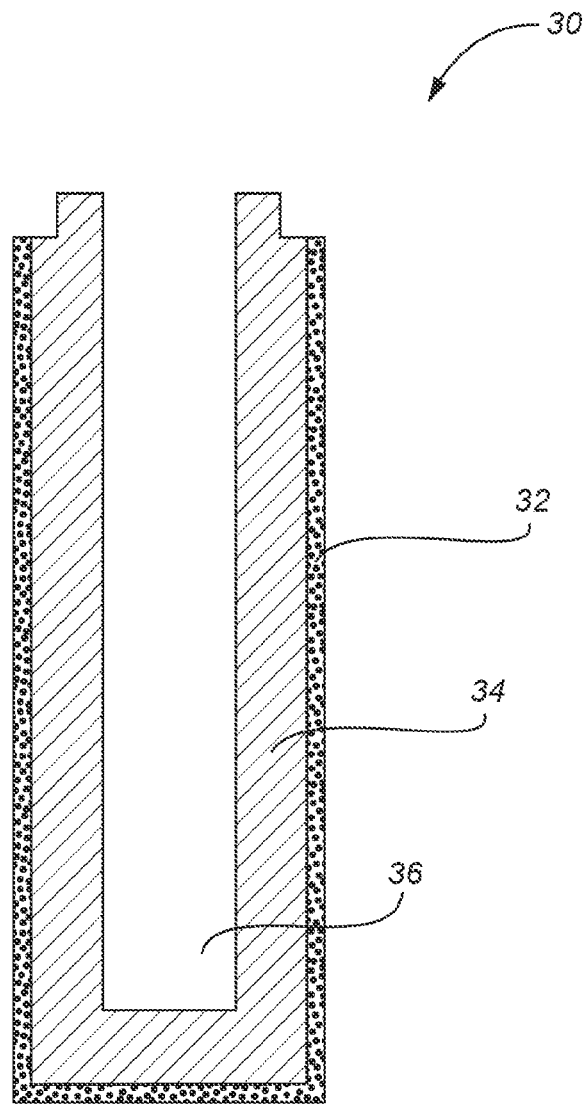
FIG. 3 is a schematic representation of one non mechanical valve 30 of the present invention showing a fluorinated polymer coated component 32 external and adjacent to a self-sealing component 34 surrounding a central cylindrical lumen 36.

In another embodiment, a porous non mechanical valve comprises a fluorinated polymer coating. In one embodiment, the fluorinated material is spray coated. The fluorinated polymers that can be coated on the devices include polytetrafluoroethylene (PTFE) or other types of perfluorinated polymers such as polyperfluoroalkyl and polyperfluoroether from Cytonix LLC (Beltsville, Md.). A PTFE solution and also aerosols may be used, such as MS-122 series, MS-136 series aerosol based mold release products, and MS 143 series and MS 145 series solution based mold release products from Miller-Stephenson (Sylmar, Calif.), or FluoroPel, FluorAcryl, Fluorothane, FluoroSyl, and FluoroTac products from Cytonix (Beltsville, Md.). In one embodiment, the fluorinated polymer coating is on the external surface of the porous non mechanical valve. In one embodiment, the fluorinated polymer coating on the external surface of the porous non mechanical valve has oleophobic properties (FIG. 3). The fluorinated polymer coating provides the porous non mechanical valve with better resistance to organic vapors and particles in the surgical fume that can cause premature vacuum shut off. The coating also prevents premature shut off caused by the foams and bubbles generated during the suction process.

Color Change Indicators

Porous non mechanical valves of the present invention additionally comprise at least one color change indicator. A color change indicator, according to embodiments of the present invention, is operable to at least partially change the color of the porous non mechanical valve when contacted with a liquid or an aerosol containing fluid. In some embodiments, the color change indicator changes the porous non mechanical valve from a first color to a second color when contacted with a liquid. In other embodiments, the color change indicator changes the porous non mechanical valve from colorless or white to colored. In a further embodiment, the color change indicator changes the porous non mechanical valve from a first shade of a color to a different shade of the same color. The color change of porous non mechanical valve, according to embodiments of the present invention, depends on the identity of the color change indicator selected.

In some embodiments, a color change indicator comprises an inorganic or organic dye, including food grade dyes, azo compounds, or azo dyes. In some embodiments, color change indicators do not comprise inorganic salts, including transition metal salts. Additionally, in some embodiments, a color change indicator does not comprise a conjugate or complex that changes color upon the binding of an analyte. In some embodiments, self-sealing barrier compositions of the present invention do not comprise proteins or other biological molecules.

Color change indicators comprising food grade dyes, according to embodiments of the present invention, are operable to be used with biological samples due to the non-toxic nature of the food dyes. In some embodiments, a color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or combinations thereof.

Color change indicators, according to some embodiments, demonstrate a pH dependency on the color produced. As a result, color change indicators, in some embodiments, indicate not only liquid contact with the barrier composition but the relative pH of the contacting liquid as well. Color change indicators demonstrating a pH dependency, in some embodiments, comprise methyl violet, eosin yellow, malachite green, thymol blue, methyl yellow, bromophenol blue, congo red, methyl orange, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or combinations thereof.

Methods of Making the Porous Non Mechanical Valves

One method of making the porous non mechanical valves of the present invention involves molding and sintering.

The plastic particles and super absorbent particles or self-sealing particles are mixed together in a percentage that provides a self-sealing product. Generally plastic particles are in the range of 50 to 95%, from 60 to 90%, from 70 to 80% wt % and super absorbent particles are in the range of 5 to 50%, 10 to 40%, 20 to 30% wt %.

The mixed particles, in some embodiments, are sintered at a temperature ranging from about 90° C. to about 260° C., or about 140° C. to about 210° C. The sintering temperature, according to embodiments of the present invention, is dependent upon and selected according to the identity of the plastic particles and is known to one of ordinary skill in the art.

The mixed particles, in some embodiments, are sintered for a time period ranging from about 30 seconds to about 30 minutes. In other embodiments, plastic particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of plastic particles is administered under ambient pressure (1 atm). In other embodiments sintering of plastic particles is administered under pressures greater than ambient pressure.

In another embodiment, the valves are not made with a sintering process. In this embodiment, the fiber based non mechanical valve may be formed by pultrusion through a heated die. The temperature and speed depend on the material formulation. The fiber is extruded in a tube or a rod form and cut into a desired length. If the fiber is in a tube form, one end of the tube can be plugged with a solid non-porous plug, a sintered porous plug, a sintered self-sealing porous plug, or a fiber plug.

Physical-Chemical Properties

In some embodiments, the pore size range of non mechanical valves of the present invention is from about 0.5 to about 400 microns, from about 1.0 to about 300 microns, from about 1.0 to about 200 microns, or from about 5.0 to about 100 microns.

In some embodiments, the pore volume range of these non mechanical valves of the present invention is from about 5% to about 90%, from about 10% to about 85%, or from about 20% to about 80%.

Different embodiments of the present application may show differences in pore shape, for example when particles are used, particles and fibers, or only fibers,

VARIOUS EMBODIMENTS

In one embodiment, the closed end of the porous non mechanical valve has a higher pore size than the other component of the non mechanical valve (FIG. 1). The higher pore size component provides the porous non mechanical valve with better resistance to surgical fumes and reduces the premature shut off, while the component with lower pore size provides better blocking of bodily fluids.

Figure 2:
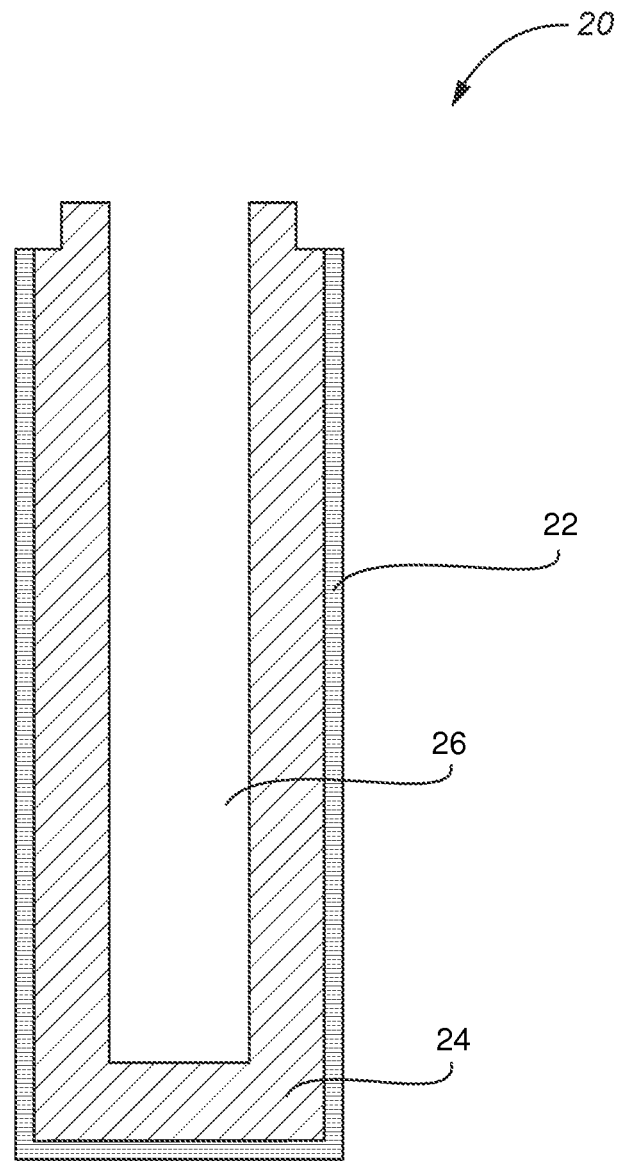
FIG. 2 is a schematic representation of one non mechanical valve 20 of the present invention showing a hydrophobic non self-sealing component 22 external and adjacent to a self-sealing component 24 surrounding a central cylindrical lumen 26.

In another embodiment, the sintered non mechanical valve comprises two components, and the two components have a different chemical composition. In one embodiment, the two components are the two surfaces (external surface and internal surface) of the non mechanical valve (FIG. 2). The external surface of the sintered non mechanical valve comprises sintered polymer particles, while the internal surface comprises both sintered polymer particles and sintered water absorbable particles. Such water absorbable materials may include materials that can absorb water more than 5, 10 or 100 times the weight of the resin, or a material which can quickly dissolve in water and form high viscosity solutions. In this case, the external layer is hydrophobic but not water absorbable and not self-sealing, while the internal layer is water absorbable and self-sealing. When the fumes containing particles and moisture or organic vapors reach the filter, the external hydrophobic layer prevents vapor or particles from penetrating into the water absorbable layer, thereby preventing premature vacuum shut off. The external layer can also prevent premature vacuum shut off caused by the foams and bubbles during the suction process in the suction canister.

In one embodiment, the porous non mechanical valve comprises a first component and a second component, wherein the first component has a different pore structure than the second component.

In another embodiment, the porous non mechanical valve comprises sintered particles of plastic and sintered superabsorbent particles.

In still another embodiment, the porous non mechanical valve comprises a first component and a second component wherein the first component has a different chemical composition than the second component.

In another embodiment, the porous non mechanical valve comprises a first component and a second component wherein the first component comprises a sintered self-sealing matrix of plastic particles and superabsorbent particles and the second component comprises a self-sealing fiber matrix comprising superabsorbent fibers.

In still another embodiment, the porous non mechanical valve comprises a first component and a second component wherein the first component comprises a sintered self-sealing matrix of plastic particles and superabsorbent particles and the second component comprises a non self-sealing fiber matrix.

In another embodiment, the porous non mechanical valve comprises a first component and a second component wherein the first component comprises a sintered non self-sealing matrix of plastic particles and the second component comprises a self-sealing fiber matrix comprising superabsorbent fibers.

In another embodiment, the porous non mechanical valve comprises a first component and a second component, wherein the first component is external to the second component, and the first component is not self-sealing and the second component is self-sealing.

In another embodiment, the porous non mechanical valve comprises a first component and a second component, wherein the first component comprises plastic bicomponent fibers and the second component comprises plastic bicomponent fibers and superabsorbent fibers.

In still another embodiment, the porous non mechanical valve comprises plastic particles, superabsorbent particles and a fluorinated polymer coating on an external surface.

In still another embodiment, the porous non mechanical valve further comprises a self-sealing additive.

In another embodiment, the porous non mechanical valve comprises plastic fibers and superabsorbent fibers.

Figure 4:
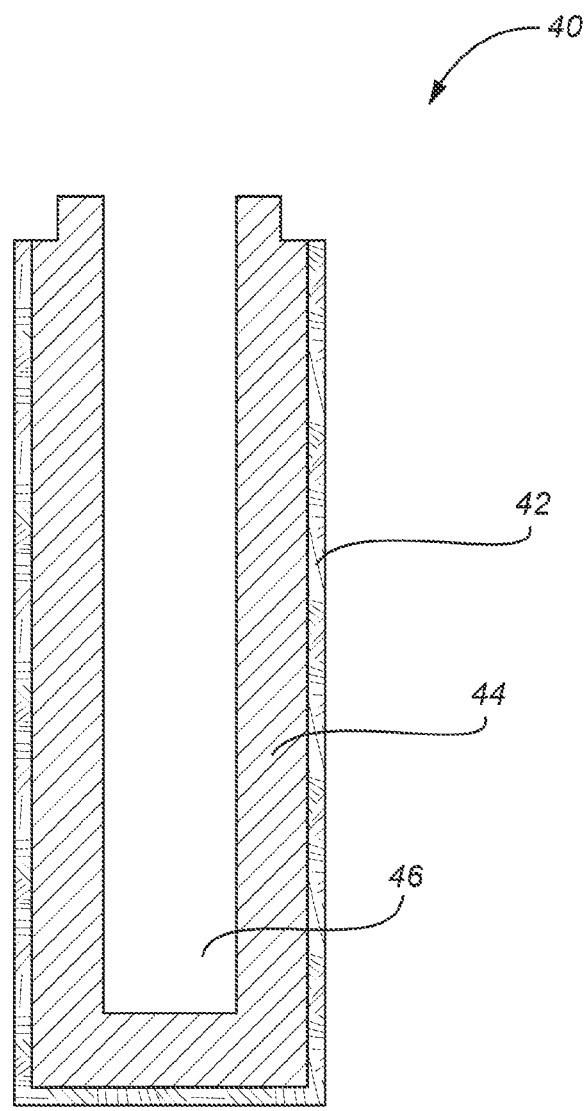
FIG. 4 is a schematic representation of one non mechanical valve 40 of the present invention showing a coalescence filtration component 42 external and adjacent to a self-sealing component 44 surrounding a central cylindrical lumen 46.
Figure 5:
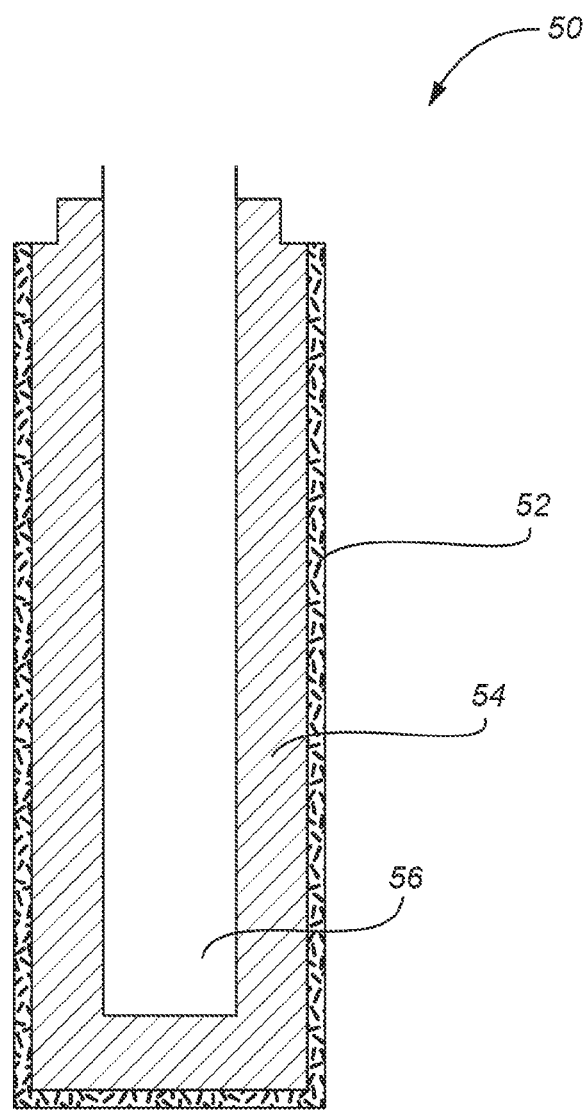
FIG. 5 is a schematic representation of one non mechanical valve 50 of the present invention showing a fabric shell component 52 external and adjacent to a self-sealing component 54 surrounding a central cylindrical lumen 56.
Figure 6A:
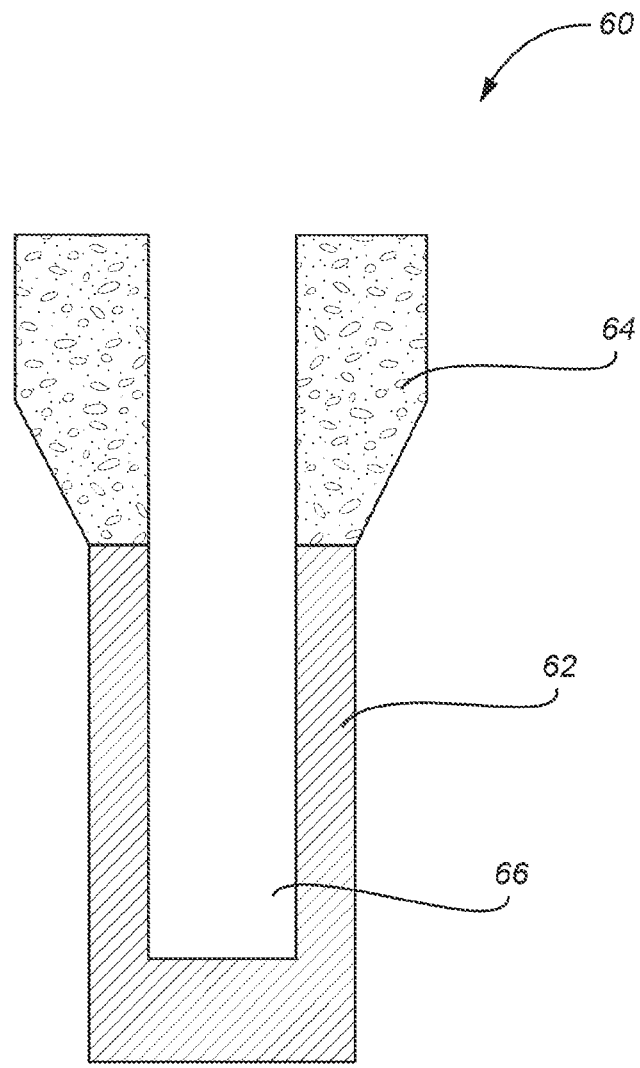
FIG. 6 A is a schematic representation of one non mechanical valve 60 of the present invention showing a first component of high permeability material 62 and a second component of low permeability material 64 surrounding a central cylindrical lumen 66.
Figure 6B:
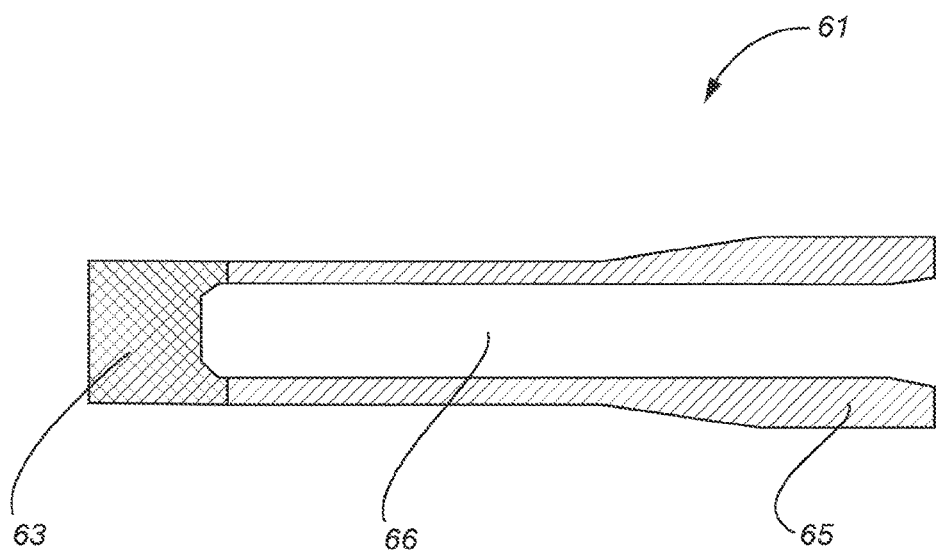
Figure 7:
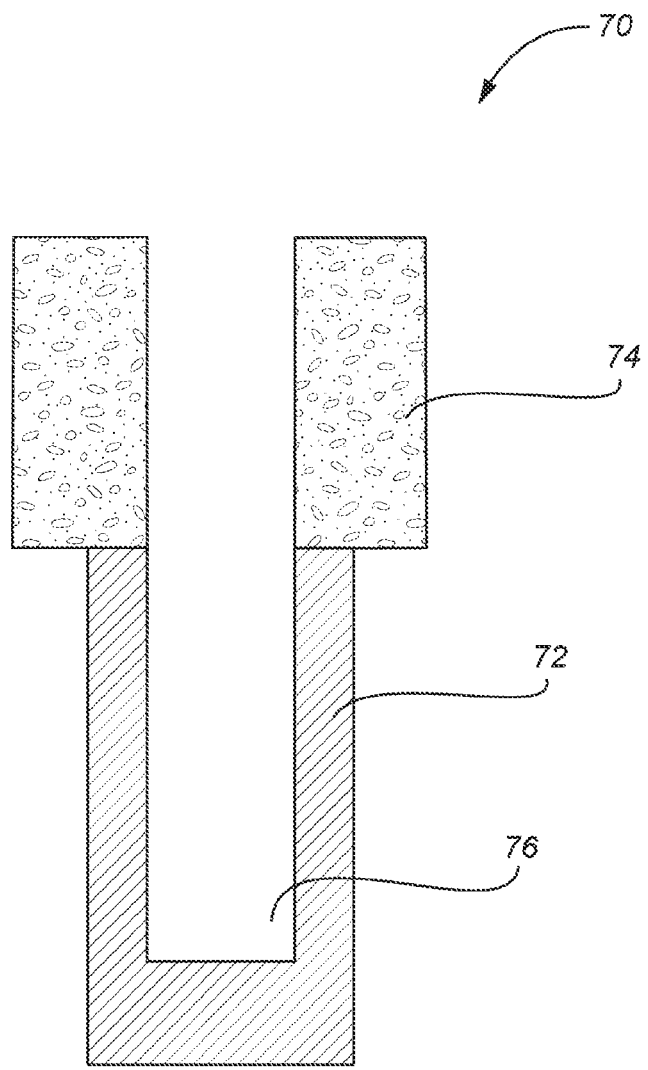
FIG. 7 is a schematic representation of one non mechanical valve 70 of the present invention showing a component of high permeability material 72 and a component of low permeability material 74 surrounding a central cylindrical lumen 76.
Figure 8:
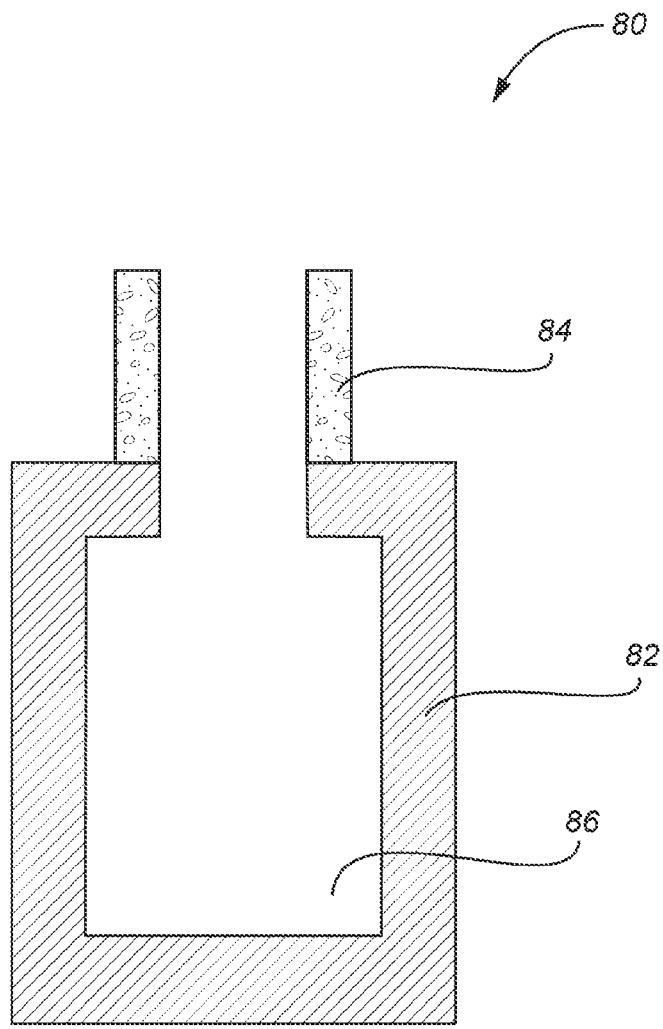
FIG. 8 is a schematic representation of one non mechanical valve 80 of the present invention showing a component of high permeability material 82 and a component of low permeability material 84 surrounding a central lumen 86.
Figure 9:
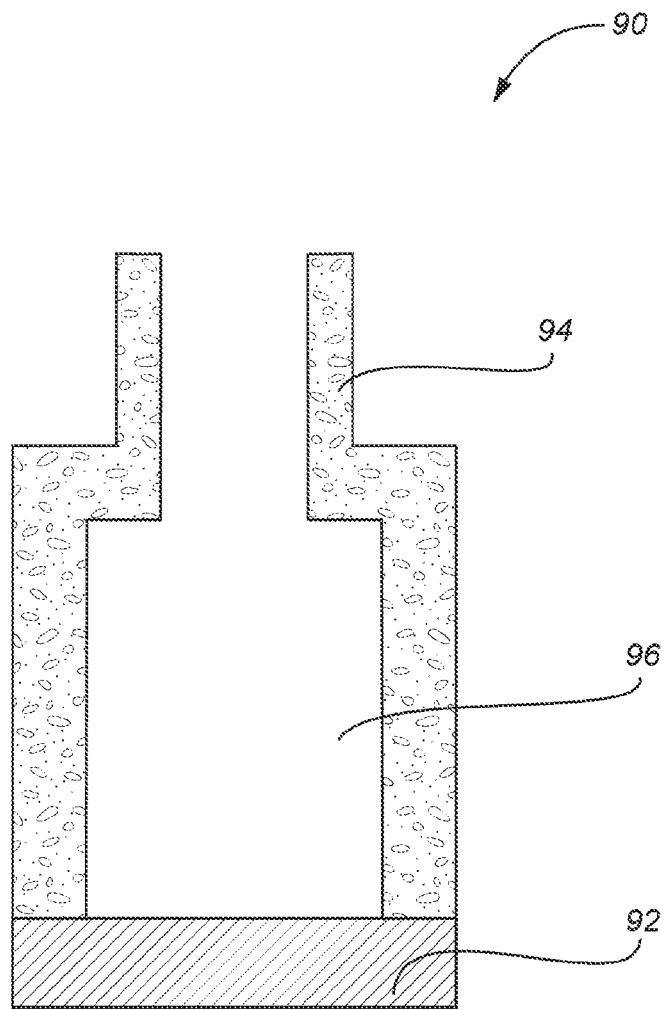
FIG. 9 is a schematic representation of one non mechanical valve 90 of the present invention showing a component of high permeability material 92 and a component of low permeability material 94 surrounding a central lumen 96.
Figure 10:
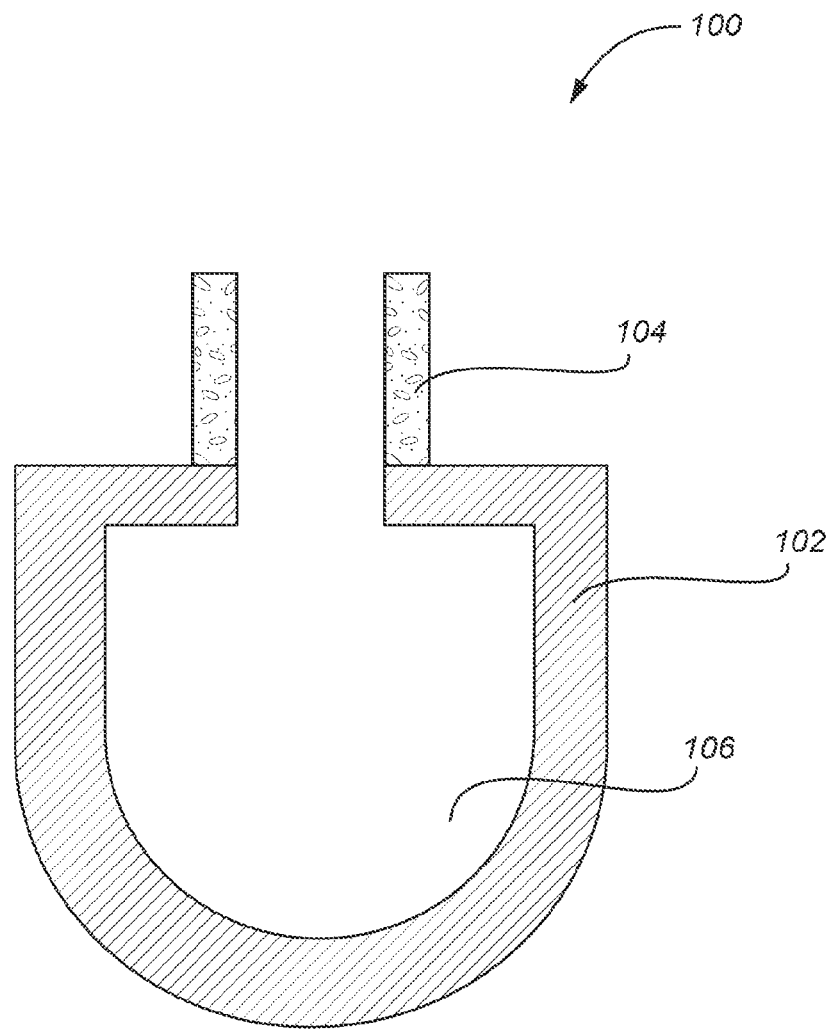
FIG. 10 is a schematic representation of one non mechanical valve 100 of the present invention showing a component of high permeability material 102 and a component of low permeability material 104 surrounding a central lumen 106.

In another embodiment, the sintered porous non mechanical valve further comprises a porous wrapping shell. The porous wrapping shell for the non mechanical valve may be a non-woven fiber, screen, or coalescence filter (FIGS. 4-5). These shells attached to the external surface of the sintered non mechanical valves for suction canisters help block particles and vapor in the surgical fume and reduce premature vacuum shut off.

In another embodiment, the non mechanical valve may also contain a deodorant component in the filter or in the hollow of the filter. Deodorant may be a fragrance, or an odor absorbing materials, such as activated carbon.

In yet another embodiment, the non mechanical valve may also contain disinfectants, or anti-microbials such as germicides, bactericidal and/or viricidal, anti-fungal or anti-protozoal compositions, in the filter or in the hollow of the filter. Such compositions are known to one of ordinary skill in the art.

In still another embodiment, the non mechanical valve may also contain a color change indicator incorporated in the first component, the second component or both the first component and the second component.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Dual Components Products with Two Regions with Different Pore Sizes

Material was loading into first part of the mold cavity (with the shape of FIG. 1) by putting the mixture of UHMWPE particles (average particle size of 150 microns) and carboxymethylcellulose (CMC) particles in the mold, evenly distributing it and then vibrating it. Next, the mixture of HDPE (average particle size of 250 microns) and CMC particles with average particle size of 120 microns was placed on the second part of mold cavity. Both processes were vibrated with pneumatic vibrators from 20-40 seconds at 20-40 psi. (1.38 to 2.76 bar).

The material was heated in the cavities up to 170° C. for about 15 minutes. Once the mold achieved 170° C., it was kept at this temperature for 10 seconds. The mold was cooled to room temperature and parts were removed from the mold. The resulting parts have two distinguishable components or regions, one component has a pore size range of 20 to 40 microns and another component has a pore size range of 70 to 90 microns.

Five of these non mechanical valves were tested for airflow and a range of values of 2.35 to 2.46 standard cubic feet per minute (SCFM) (66-70 liter per minute) at −1.0 inches of Hg (−33 mbar) vacuum were measured. Water entry was tested at −27 inches of Hg (−914 mbar) vacuum and all five valves passed the test and did not permit water to pass through. Negative pressure in this and the following examples means the pressure inside the non mechanical valve is lower than ambient atmosphere pressure.

Example 2

Non-Mechanical Valve with Self-Sealing Internal Surface and Hydrophobic External Surface The mixture of UHMWPE particles (average particle size of 150 microns) and CMC particles was loaded in the mold cavity, evenly distributed and then vibrated. The material was heated in the cavities up to 170° C. for about 15 minutes. Once the mold achieved 170° C., it was kept at this temperature for 10 seconds. The mold was cooled to room temperature and parts were removed from the mold. The resulting parts had a pore size range of 20 to 40 microns. This self-sealing part was used as an internal part of the non-mechanical valve.

Next, the self-sealing part made above was put into another mold cavity with 1 mm larger diameter and 0.5 mm deeper. UHMWPE (average particle size of 150 microns) particles were filled in the gaps between the self-sealing part and the mold wall, and mold was vibrated with pneumatic vibrators from 20-40 seconds at 20-40 psi. (1.38-2.76 bar)

The material was heated in the cavities up to 170° C. for about 5 minutes. Once the mold achieved 170° C., it was kept at this temperature for 10 seconds. The mold was cooled to room temperature and parts were removed from the mold. The resulting parts had two distinguishable components, one component was an internal region with a pore size range of 20 to 40 microns with self-sealing properties, and an external hydrophobic component with a pore size range of 20 to 40 microns. The part had a shape shown in FIG. 2, about 42 mm in length, 13.5 mm in diameter, and a wall thickness of 3 mm. The parts had an average of air flow about 50 standard cubic feet per hour at −4.75 inches of Hg. (24 liter per minute at −160 mbar). Water entry was also tested at −27 inches of Hg (−914 mbar) vacuum. The parts passed the test and did not permit water to pass through.

Example 3

Non-Mechanical Valve with Fluorinated Polymer Coating on Our Surface

A mixture of HDPE particles (average particle size of 150 microns) and carboxymethylcellulose (CMC) particles was loaded in the mold cavity, evenly distributed and then vibrated. The material was heated in the cavity up to 170° C. for about 15 minutes. Once the mold achieved 170° C., it was kept at this temperature for 10 seconds. The mold was cooled to room temperature and parts were removed from the mold. The resulting parts had a pore size range of 20 to 40 microns. The part had a cylindrical shape, 42 mm in length, 13.5 mm in diameter, and a wall thickness of 3 mm. The parts had an average air flow of about 50 standard cubic feet per hour at −1.65 inches of Hg. (24 liter per minute at −56 mbar).

The external surface part was then spray coated with 2% FluoroPel solution (Cytonix, Beltville, Md.). The coated part was allowed to dry at room temperature. The water contact angle was over 90 degrees at the external surface. The coated parts had an average of air flow of about 50 standard cubic feet per hour at −5 inches of Hg. (24 liter per minute at −169 mbar). Water entry was also tested at −27 inches of Hg (−914 mbar) vacuum. The coated parts passed the test and did not permit water to pass through.

Example 4

Non-Mechanical Valve with PTFE Based Mold Release Agent Coating its Surface

A mixture of UHMWPE particles (average particle size of 150 microns) and carboxymethylcellulose (CMC) particles was loaded in the mold cavity, evenly distributed and then vibrated. The material was heated in the cavities up to 170° C. for about 15 minutes. Once the mold achieved 170° C., it was kept at this temperature for 10 seconds. The mold was cooled to room temperature and parts were removed from the mold. The resulting parts had a pore size range of 20 to 40 microns. The parts had a cylinder shape, 42 mm in length, 13.5 mm in diameter, and a wall thickness of 3 mm. The parts had an average air flow of about 50 standard cubic feet per hour at −1.65 inches of Hg. (24 liter per minute at −56 mbar)

The external surface part was then spray coated with MS-122AD mold release aerosol. The coated part was allowed to dry at room temperature. The water contact angle was over 90 degrees at the external surface. The parts had an average air flow of about 50 standard cubic feet per hour at −2 inches of Hg. (24 liter per minute at −67 mbar). Water entry was also tested at −27 inches of Hg (−914 mbar) vacuum. The coated parts passed the test and did not permit water to pass through.

Example 5

Fiber Non-Mechanical Valve with Biodegradable Bicomponent Fiber and Superabsorbent Fiber The non-mechanical valve is made by pultrusion of a synthetic sinterable poly(lactic acid) (PLA) or its copolymer in concentric bicomponent fibers (70%) with an Oasis® superabsorbent fiber (30%) (wt %). In a specific embodiment, both the core and the sheath of bicomponent materials are PLA and the core PLA has a melting temperature higher than the melting temperature of the sheath PLA (Far Eastern Textile Ltd. Hong Kong or China) Ingeo SLN2450CM, 4 deniers). It is preferred that the melting temperature difference between the core and sheath is more than 10° C., more than 20° C. or more than 30° C. The melting temperature of the polymer can be controlled by manipulation of crystallization, the copolymerization or the blend as known to one of ordinary skill in the art of polymer chemistry. The superabsorbent fibers are from $M^2$ Polymer technologies, Inc. (West Dundee, Ill., USA).

30 lb of Oasis® superabsorbent fiber and 70 lb of PLA/PLA bicomponent fiber (Far Eastern Textile Ltd. Hong Kong or China) Ingeo SLN2450CM, 4 denier) are blended and carded into sliver of 25 grains by a Hollingsworth Mini-Carder. The length of Oasis® superabsorbent fiber is 52 mm, and its diameter is 5.0 deniers. The length of PLA staple is 52 mm, and its diameter is 4.0 deniers.

The blended sliver are bonded together to form fiber self-sealing rod by using an oven pultrusion process. The blended slivers are pultruded through an oven at the temperature of 204-221° C. and compressed through a die at the temperature of 35-100° C. The pultrusion speed is 5 to 10 mm/second. This process produces a cylindrical porous self-sealing fiber matrix. A die compresses and shapes this matrix into rods that are subsequently air cooled and cut to length.

Example 6

Fiber Non-Mechanical Valve with Polyethylene/Polypropylene Bicomponent Fiber and Superabsorbent Fiber The non-mechanical valve is made from pultrusion of synthetic sinterable polyethylene/polypropylene (PE/PP) concentric bicomponent fiber (70%) from FiberVisions (Duluth, Ga.) with an Oasis® superabsorbent fiber (30%) (wt). The superabsorbent fibers are from $M^2$ Polymer technologies, Inc. (West Dundee, Ill., USA).

30 lb of Oasis® superabsorbent fiber and 70 lb of polyethylene/polypropylene (PE/PP) concentric bicomponent fiber are blended and carded into sliver of 25 grains by a Hollingsworth Mini-Carder. The length of Oasis® superabsorbent fiber is 52 mm, and its diameter is 5.0 denier. The length of polyethylene/polypropylene (PE/PP) concentric bicomponent fiber staple is 52 mm, and its diameter is 6.0 denier.

The blended sliver are bonded together to form fiber self-sealing rod by using an oven pultrusion process. The bicomponent fibers are composed of a concentric sheath and core material. To facilitate sintering, the sheath material has a lower melting point than the core material. The oven thermally bonds (melts) the sheath material of the bicomponent fibers to other bicomponent fibers and to the superabsorbent fibers. The silver is pultruded through an oven at the temperature of 125-170° C. and compressed through a die at the temperature of 35-100° C. The pultrusion speed is 2.5 to 10 mm/second This process produces a cylindrical self-sealing porous fiber matrix. A die compresses and shape this matrix into rods that are subsequently air cooled and cut to length.

Example 7

Fiber Non-Mechanical Valve with Polyethylene/Polyester Bicomponent Fiber and Superabsorbent Fiber The non-mechanical valve is made from pultrusion of synthetic sinterable polyethylene/polyester (PE/PET) concentric bicomponent fiber (70%) from FiberVisions (Duluth, Ga.) with an Oasis® superabsorbent fiber (30%) (wt). The superabsorbent fibers are from $M^2$ Polymer technologies, Inc. (West Dundee, Ill., USA).

30 lb of Oasis® superabsorbent fiber and 70 lb of polyethylene/polyester (PE/PET) concentric bicomponent fiber are blended and carded into sliver of 25 grains by a Hollingsworth Mini-Carder. The length of Oasis® superabsorbent fiber is 52 mm, and its diameter is 5.0 denier. The length of polyethylene/polyester (PE/PET) concentric bicomponent fiber staple is 52 mm, and its diameter is 6.0 denier.

The blended sliver are bonded together to form fiber self-sealing rod by using an oven pultrusion process. The bicomponent fibers are composed of a concentric sheath and core material. To facilitate sintering, the sheath material is of a lower melting point than the core material. The oven thermally bonds (melts) the sheath material of the bicomponent fibers to other bicomponent fibers and to the superabsorbent fibers. The silver is pultruded through an oven at the temperature of 175-220° C. and compressed through a die at the temperature of 35-100° C. The pultrusion speed is 2.5 to 10 mm/second. This process produces a cylindrical self-sealing porous fiber matrix. A die compresses and shape this matrix into rods that are subsequently air cooled and cut to length.

Example 8

Fiber Non-Mechanical Valve with Non Self-Sealing Bicomponent Fiber Sheath and Self-Sealing Core Comprising Superabsorbent Fiber The non-mechanical valve core is made from pultrusion of synthetic sinterable polyethylene/polyester (PE/PET) concentric bicomponent fiber (50%) from FiberVisions (Duluth, Ga.) with an Oasis® superabsorbent fiber (50%) (wt). The superabsorbent fibers are from $M^2$ Polymer technologies, Inc. (West Dundee, Ill., USA).

50 lb of Oasis® superabsorbent fiber and 50 lb of polyethylene/polyester (PE/PET) concentric bicomponent fiber are blended and carded into sliver of 25 grains by a Hollingsworth Mini-Carder. The length of Oasis® superabsorbent fiber is 52 mm, and its diameter is 5.0 denier. The length of polyethylene/polyester (PE/PET) concentric bicomponent fiber staple is 52 mm, and its diameter is 6.0 denier.

The blended slivers are bonded together to form fiber self-sealing rod by using an oven pultrusion process. The silver is pultruded through an oven at the temperature of 175-220° C. and compressed through a 10 mm die at the temperature of 35-100° C. The pultrusion speed is 2.5 to 10 mm/second. This process produces a cylindrical self-sealing porous fiber rod with diameter of 10 mm.

Polyethylene/polyester (PE/PET) concentric bicomponent fibers are carded into sliver of 25 grains by a Hollingsworth Mini-Carder. The length of polyethylene/polyester (PE/PET) concentric bicomponent fiber staple is 52 mm, and its diameter is 6.0 denier.

The 10 mm diameter self-sealing rod and PE/PET sliver are co-pultruded through an oven at the temperature of 175-220° C. and compressed through a 15 mm die at the temperature of 35-100° C. The self-sealing rod is in the center of die and with PE/PET fiber around it. The pultrusion speed is 5 to 10 mm/second. This process produces a cylindrical self-sealing porous fiber rod with diameter of 15 mm with center 10 mm with self-sealing component and out 2.5 mm sheath non self-sealing fiber component.

Example 9

Fiber Non-Mechanical Valve with Non Self-Sealing Bicomponent Fiber Sheath and Self-Sealing Core Comprising Superabsorbent Fiber Self-sealing sliver is made from carding the blend of 70 lb of Oasis® superabsorbent fiber and 30 lb of sinterable polyethylene/polyester (PE/PET) concentric bicomponent fiber by a Hollingsworth Mini-Carder. The sliver is 25 grams. PE/PET sliver is made from carding sinterable polyethylene/polyester (PE/PET) concentric bicomponent fiber by a Hollingsworth Mini-Carder. The sliver is 25 grams. The length of Oasis® superabsorbent fiber is 52 mm, and its diameter is 5.0 denier. The length of polyethylene/polyester (PE/PET) concentric bicomponent fiber staple is 52 mm, and its diameter is 6.0 denier.

The self-sealing silver and PE/PET sliver are co-pultruded through an oven at the temperature of 175-220° C. and compressed through a die at the temperature of 35-100° C. The self-sealing sliver is pultruded in the center of die and PE/PET sliver is pultruded on the edge of the die. The pultrusion speed is 2.5 to 10 mm/second. This produces a cylindrical self-sealing porous fiber rod with self-sealing component in the center and a non self-sealing sheath.

Example 10

Fiber Non-Mechanical Valve with Sandwich Layered Structure with Non Self-Sealing Bicomponent Fiber Outer Layer and Self-Sealing Middle Layer Self-sealing sliver is made from carding the blend of 70 lb of Oasis® superabsorbent fiber and 30 lb of sinterable polyethylene/polyester (PE/PET) concentric bicomponent fiber by a Hollingsworth Mini-Carder. The sliver is 25 grams. PE/PET sliver is made from carding sinterable polyethylene/polyester (PE/PET) concentric bicomponent fiber by a Hollingsworth Mini-Carder. The sliver is 25 grams. The length of Oasis® superabsorbent fiber is 52 mm, and its diameter is 5.0 denier. The length of polyethylene/polyester (PE/PET) concentric bicomponent fiber staple is 52 mm, and its diameter is 6.0 denier.

The self-sealing sliver and PE/PET sliver are co-pultruded through an oven at the temperature of 175-220° C. and compressed through a sheet die at the temperature of 35-100° C. The self-sealing sliver is pultruded in the center of die and PE/PET sliver is pultruded on the both sides of self-sealing sliver. The pultrusion speed is 2.5 to 10 mm/second. This produces a sheet form self-sealing porous fiber with self-sealing component in the center and a non self-sealing on both sides. The thickness of sheet can be from 3 mm to 15 mm, and thickness of self-sealing layer varies from 2 mm to 13 mm. The sheet can be die cut into disk or other form to fit and device design.

Example 11

Composite Non-Mechanical Valve Comprising a Polyethylene/Polyester Bicomponent Fiber and Superabsorbent Fiber Tube and Porous Plastic Self-Sealing Plugs The non-mechanical valve is made from pultrusion of synthetic sinterable polyethylene/polyester (PE/PET) concentric bicomponent fiber (70%) from FiberVisions (Duluth, Ga.) with an Oasis® superabsorbent fiber (30%) (wt). The superabsorbent fibers are from $M^2$ Polymer technologies, Inc. (West Dundee, Ill., USA).

30 lb of Oasis® superabsorbent fiber and 70 lb of polyethylene/polyester (PE/PET) concentric bicomponent fiber are blended and carded into sliver of 25 grains by a Hollingsworth Mini-Carder. The length of Oasis® superabsorbent fiber is 52 mm, and its diameter is 5.0 denier. The length of polyethylene/polyester (PE/PET) concentric bicomponent fiber staple is 52 mm, and its diameter is 6.0 denier.

The blended slivers are bonded together to form fiber self-sealing tube by using an oven pultrusion process. The bicomponent fibers are composed of a concentric sheath and core material. To facilitate sintering, the sheath material is of a lower melting point than the core material. The oven thermally bonded (melted) the sheath material of the bicomponent fibers to other bicomponent fibers and to the superabsorbent fibers. The silver is pultruded through an oven at the temperature of 175-220° C. and compressed through a die at the temperature of 35-100° C. The pultrusion speed is 2.5 to 10 mm/second. This process produces a cylindrical self-sealing porous fiber tube matrix. A die compresses and shape this matrix into tubes that are subsequently air cooled and cut to length. The tubes can have different external diameters and internal diameters. As an example, a tube has a 25 mm external diameter and 10 mm internal diameter. A sintered porous self-sealing plug with a diameter of 10 mm and 5 mm in thickness is plugged into the fiber self-sealing tube to form a composite non mechanical valve with a hollowed structure and an open end and a closed end.

Example 12

Composite Non-Mechanical Valve Comprising Polyethylene/Polyester Bicomponent Fiber and Superabsorbent Fiber Rod Core and a Hydrophobic Non Self-Sealing Porous Plastic Sheath UHMWPE particles (average particle size of 150 microns) are loaded into a tube mold and sintered at 170° C. for about 5 minutes. The mold is cooled to room temperature and parts removed from the mold. The resulting hydrophobic porous plastic tubes have an average pore size of about 30 microns and pore volume of about 40%. The tube can have different external and internal diameters.

The fiber self-sealing rods are made as disclosed in examples 5 to 7 above are inserted into the porous plastic tube. The fiber self-sealing rods have diameters about the same as the internal diameter of the sintered hydrophobic non self-sealing tube. The resulted composite non mechanical valve has a hydrophobic non self-sealing porous plastic sheath and a fiber self-sealing core.

Example 13

Multi-Component Non Mechanical Valve Prevents Premature Shut Off

A sintered single component self-sealing porous plastic non mechanical valve (as disclosed in example 4 before the MS-122AD fluoropolymer coating), a fluoropolymer coated single component self-sealing porous plastic non mechanical valve (as disclosed in example 4) and a dual layer self-sealing porous plastic non mechanical valve (as disclosed in example 2), were compared for pressure drop and air flow change before and after dipping into water. The pressure drops at 50 SCFH were recorded before the parts were dipped into the water. The parts were dipped into water for 5 seconds to an extent that 90% of the surface areas were immersed into the water. The pressure drops were recorded immediately after the parts were removed from the water. Table 1 shows the pressure drop change before and after dipping into the water. The data indicated that dual composition non-mechanical valve could prevent premature pressure drop due to container trip or water flush.

TABLE 1

Single component non-mechanical valve, fluoropolymer coated non-mechanical valve and dual layer non-mechanical valve pressure drop change before and after dipping into water for 5 seconds. Pressure drops were measured at 24 liter per minute of air flow expressed in mbar.

| Single component | | | Fluoropolymer coated | | | Dual layer | | |
| --- | --- | --- | --- | --- | --- | --- | --- | --- |
| Before | After | Change | Before | After | Change | Before | After | Change |
| 61.2 | 476 | 414.8 | 63.24 | 226.1 | 162.86 | 173.4 | 178.5 | 5.1 |
| 63.58 | 340 | 276.42 | 79.56 | 309.06 | 229.5 | 157.76 | 188.36 | 30.6 |
| 57.12 | 438.6 | 381.48 | 63.58 | 302.26 | 238.68 | 163.2 | 168.98 | 5.78 |
| 79.22 | 578 | 498.78 | 66.3 | 218.28 | 151.98 | 119 | 139.4 | 20.4 |
| 52.7 | 294.1 | 241.4 | 88.06 | 340 | 251.94 | 195.16 | 217.6 | 22.44 |

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

What is claimed is:

1. A porous non mechanical valve comprising an internal component and an external component, the external component comprising a hydrophobic, sintered, non self-sealing component, the external component sintered to and co-molded with and over the internal component,
the internal component comprising a sintered, porous self-sealing component, the internal component shaped to define a central cylindrical lumen,
wherein the external component and the internal component comprise different pore sizes, the external component comprising a pore size in a range of 20-40 microns, wherein the external component comprises a smaller pore size than the internal self-sealing component,
wherein the porous non mechanical valve blocks or retards the flow of liquid through the porous non mechanical valve.

2. The porous non mechanical valve of claim 1, wherein the internal component comprises a sintered self-sealing matrix of plastic particles and superabsorbent particles and the external component comprises a non self-sealing fiber matrix.

3. The porous non mechanical valve of claim 1, comprising a fluorinated polymer coating on an external surface of the external component of the porous non mechanical valve.

4. The porous non mechanical valve of claim 2, wherein the plastic particles are polyolefin, polyester or nylon particles.

5. The porous non mechanical valve of claim 4, wherein the polyolefin plastic particles are polyethylene, high density polyethylene, ultrahigh molecular weight polyethylene or polypropylene.

6. The porous non mechanical valve of claim 2, wherein the non self-sealing fiber matrix comprises polyethylene (PE)/polyethylene terephthalate (PET), polypropylene (PP)/PET, co-polyester/PET, PE/Nylon, PP/Nylon, Nylon/Nylon, PE/PP, or PET/PP bicomponent fibers.

7. The porous non mechanical valve of claim 2, wherein the superabsorbent particles are carboxyl methyl cellulose (CMC), hydroxypropyl cellulose (HPC), hydrolyzed starch, acrylonitrile graft copolymer, neutralized starch-acrylic acid graft copolymer, saponified acrylic acid ester-vinyl acetate copolymer, hydrolyzed acrylonitrile copolymer, acrylamide copolymer, modified cross-linked polyvinyl alcohol, neutralized self-crosslinking polyacrylic acid, crosslinked polyacrylate salts, neutralized crosslinked isobutylene-maleic anhydride copolymers, and salts and mixtures thereof, polyacrylic acids, sodium polyacrylic acid and the sodium salt of poly(2-propenamide-co-2-propenoic acid), alginates, Guar gum, Xanthan gum, Konjac gum, Tara gum or agars.

8. The porous non mechanical valve of claim 1, further comprising a color change indicator, an anti-microbial, a disinfectant, a deodorant or a combination thereof.

9. The porous non mechanical valve of claim 1, wherein the internal component comprises a sintered self-sealing matrix of plastic particles and superabsorbent particles and the external component comprises a hydrophobic, sintered, non self-sealing matrix of plastic particles.

10. The porous non mechanical valve of claim 9, wherein the plastic particles are polyolefin, polyester or nylon particles.

11. The porous non mechanical valve of claim 10, wherein the polyolefin plastic particles are polyethylene, high density polyethylene, ultrahigh molecular weight polyethylene or polypropylene.

12. The porous non mechanical valve of claim 9, wherein the superabsorbent particles are carboxyl methyl cellulose (CMC), hydroxypropyl cellulose (HPC), hydrolyzed starch, acrylonitrile graft copolymer, neutralized starch-acrylic acid graft copolymer, saponified acrylic acid ester-vinyl acetate copolymer, hydrolyzed acrylonitrile copolymer, acrylamide copolymer, modified cross-linked polyvinyl alcohol, neutralized self-crosslinking polyacrylic acid, crosslinked polyacrylate salts, neutralized crosslinked isobutylene-maleic anhydride copolymers, and salts and mixtures thereof, polyacrylic acids, sodium polyacrylic acid and the sodium salt of poly(2-propenamide-co-2-propenoic acid), alginates, Guar gum, Xanthan gum, Konjac gum, Tara gum or agars.

13. The porous non mechanical valve of claim 1, wherein the external component is porous, the internal component is porous, and the porous external component has a different pore structure and/or chemical composition than the porous internal component.

14. The porous non mechanical valve of claim 1, wherein the external component is in contact with the internal component.

15. The porous non mechanical valve of claim 1, wherein the external component is adjacent to the internal component.

16. A method of reducing clogging of a vacuum suction device comprising:
inserting the porous non mechanical valve of claim 1 into the vacuum suction device;
applying a vacuum across the porous non mechanical valve; and,
permitting fluid or moisture to contact the porous non mechanical valve, wherein passage of the fluid or moisture through the porous non mechanical valve is retarded or prevented by the porous non mechanical valve.

17. A vacuum suction device comprising the porous non-mechanical valve of claim 1.

* * * * *